(12) United States Patent
Malinowski

(10) Patent No.: US 10,160,609 B2
(45) Date of Patent: Dec. 25, 2018

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Michal Malinowski, Backnang (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 10 days.

(21) Appl. No.: 15/276,827

(22) Filed: Sep. 27, 2016

(65) Prior Publication Data

US 2017/0101277 A1    Apr. 13, 2017

(30) Foreign Application Priority Data

Oct. 13, 2015 (EP) .................................. 15189525

(51) Int. Cl.
*B65G 54/02* (2006.01)
*G01N 35/04* (2006.01)

(52) U.S. Cl.
CPC .............. *B65G 54/02* (2013.01); *G01N 35/04* (2013.01); *B65G 2201/0261* (2013.01); *G01N 2035/0406* (2013.01); *G01N 2035/0477* (2013.01)

(58) Field of Classification Search
CPC ............ B65G 54/02; B65G 2201/0261; G01N 35/04; G01N 2035/0406; G01N 2035/0477
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Gene O Crawford
*Assistant Examiner* — Keith R Campbell
(74) *Attorney, Agent, or Firm* — Roche Diagnostics Operations, Inc.

(57) ABSTRACT

A laboratory sample distribution system and a laboratory automation system are presented. The laboratory automation system comprises a laboratory sample distribution system. The laboratory sample distribution system comprises a plurality of electro-magnetic actuators. Each electro-magnetic actuator comprises a ferromagnetic core and an excitation winding. Each excitation winding exceeds its assigned ferromagnetic core.

20 Claims, 2 Drawing Sheets

(56) References Cited

U.S. PATENT DOCUMENTS

| | | | |
|---|---|---|---|
| 5,735,387 A | 4/1998 | Polaniec et al. | |
| 5,788,929 A | 8/1998 | Nesti | |
| 6,045,319 A * | 4/2000 | Uchida | B65G 54/02 112/DIG. 2 |
| 6,062,398 A | 5/2000 | Thalmayr | |
| 6,141,602 A | 10/2000 | Igarashi et al. | |
| 6,151,535 A | 11/2000 | Ehlers | |
| 6,184,596 B1 | 2/2001 | Ohzeki | |
| 6,191,507 B1 | 2/2001 | Peltier et al. | |
| 6,206,176 B1 | 3/2001 | Blonigan et al. | |
| 6,255,614 B1 | 7/2001 | Yamakawa et al. | |
| 6,260,360 B1 | 7/2001 | Wheeler | |
| 6,279,728 B1 | 8/2001 | Jung et al. | |
| 6,293,750 B1 | 9/2001 | Cohen et al. | |
| 6,429,016 B1 | 8/2002 | McNeil | |
| 6,444,171 B1 | 9/2002 | Sakazume et al. | |
| 6,571,934 B1 | 6/2003 | Thompson et al. | |
| 7,028,831 B2 | 4/2006 | Veiner | |
| 7,078,082 B2 | 7/2006 | Adams | |
| 7,122,158 B2 | 10/2006 | Itoh | |
| 7,278,532 B2 | 10/2007 | Martin | |
| 7,326,565 B2 | 2/2008 | Yokoi et al. | |
| 7,425,305 B2 | 9/2008 | Itoh | |
| 7,428,957 B2 | 9/2008 | Schaefer | |
| 7,578,383 B2 | 8/2009 | Itoh | |
| 7,597,187 B2 | 10/2009 | Bausenwein et al. | |
| 7,850,914 B2 | 12/2010 | Veiner et al. | |
| 7,858,033 B2 | 12/2010 | Itoh | |
| 7,875,254 B2 | 1/2011 | Garton et al. | |
| 7,939,484 B1 | 5/2011 | Loeffler et al. | |
| 8,240,460 B1 | 8/2012 | Bleau et al. | |
| 8,281,888 B2 | 10/2012 | Bergmann | |
| 8,502,422 B2 | 8/2013 | Lykkegaard | |
| 8,796,186 B2 | 8/2014 | Shirazi | |
| 8,833,544 B2 | 9/2014 | Stoeckle et al. | |
| 9,097,691 B2 | 8/2015 | Onizawa et al. | |
| 9,187,268 B2 | 11/2015 | Denninger et al. | |
| 9,211,543 B2 | 12/2015 | Ohga et al. | |
| 9,239,335 B2 | 1/2016 | Heise et al. | |
| 9,423,410 B2 | 8/2016 | Buehr | |
| 9,423,411 B2 | 8/2016 | Riether | |
| 9,618,525 B2 * | 4/2017 | Malinowski | G01N 35/04 |
| 2002/0009391 A1 | 1/2002 | Marquiss et al. | |
| 2003/0092185 A1 | 5/2003 | Qureshi et al. | |
| 2004/0050836 A1 | 3/2004 | Nesbitt et al. | |
| 2004/0084531 A1 | 5/2004 | Itoh | |
| 2005/0061622 A1 | 3/2005 | Martin | |
| 2005/0109580 A1 | 5/2005 | Thompson | |
| 2005/0194333 A1 | 9/2005 | Veiner et al. | |
| 2005/0196320 A1 | 9/2005 | Veiner et al. | |
| 2005/0226770 A1 | 10/2005 | Allen et al. | |
| 2005/0242963 A1 | 11/2005 | Oldham et al. | |
| 2005/0247790 A1 | 11/2005 | Itoh | |
| 2005/0260101 A1 | 11/2005 | Nauck et al. | |
| 2005/0271555 A1 | 12/2005 | Itoh | |
| 2006/0000296 A1 | 1/2006 | Salter | |
| 2006/0047303 A1 | 3/2006 | Ortiz et al. | |
| 2006/0219524 A1 | 10/2006 | Kelly et al. | |
| 2007/0116611 A1 | 5/2007 | DeMarco | |
| 2007/0210090 A1 | 9/2007 | Sixt et al. | |
| 2007/0248496 A1 | 10/2007 | Bondioli et al. | |
| 2007/0276558 A1 | 11/2007 | Kim | |
| 2008/0012511 A1 * | 1/2008 | Ono | G03F 7/70758 318/35 |
| 2008/0029368 A1 | 2/2008 | Komori | |
| 2008/0056328 A1 | 3/2008 | Rund et al. | |
| 2008/0131961 A1 | 6/2008 | Crees et al. | |
| 2009/0004732 A1 | 1/2009 | LaBarre et al. | |
| 2009/0022625 A1 | 1/2009 | Lee et al. | |
| 2009/0081771 A1 | 3/2009 | Breidford et al. | |
| 2009/0128139 A1 | 5/2009 | Drenth et al. | |
| 2009/0142844 A1 | 6/2009 | Le Comte | |
| 2009/0180931 A1 | 7/2009 | Silbert et al. | |
| 2009/0322486 A1 | 12/2009 | Gerstel | |
| 2010/0000250 A1 | 1/2010 | Sixt | |
| 2010/0152895 A1 | 6/2010 | Dai | |
| 2010/0175943 A1 | 7/2010 | Bergmann | |
| 2010/0186618 A1 | 7/2010 | King et al. | |
| 2010/0255529 A1 | 10/2010 | Cocola et al. | |
| 2010/0300831 A1 | 12/2010 | Pedrazzini | |
| 2010/0312379 A1 | 12/2010 | Pedrazzini | |
| 2011/0050213 A1 | 3/2011 | Furukawa | |
| 2011/0124038 A1 | 5/2011 | Bishop et al. | |
| 2011/0172128 A1 | 7/2011 | Davies et al. | |
| 2011/0186406 A1 | 8/2011 | Kraus et al. | |
| 2011/0287447 A1 | 11/2011 | Norderhaug et al. | |
| 2012/0037696 A1 | 2/2012 | Lavi | |
| 2012/0129673 A1 | 5/2012 | Fukugaki et al. | |
| 2012/0178170 A1 | 7/2012 | Van Praet | |
| 2012/0211645 A1 | 8/2012 | Tullo et al. | |
| 2012/0275885 A1 | 11/2012 | Furrer et al. | |
| 2012/0282683 A1 | 11/2012 | Mototsu | |
| 2012/0295358 A1 | 11/2012 | Ariff et al. | |
| 2012/0310401 A1 | 12/2012 | Shah | |
| 2013/0009731 A1 | 1/2013 | Fong et al. | |
| 2013/0034410 A1 | 2/2013 | Heise et al. | |
| 2013/0126302 A1 | 5/2013 | Johns et al. | |
| 2013/0153677 A1 | 6/2013 | Leen et al. | |
| 2013/0180824 A1 | 7/2013 | Kleinikkink et al. | |
| 2013/0263622 A1 | 10/2013 | Mullen et al. | |
| 2013/0322992 A1 | 12/2013 | Pedrazzini | |
| 2014/0170023 A1 | 6/2014 | Saito et al. | |
| 2014/0231217 A1 * | 8/2014 | Denninger | B65G 54/02 198/358 |
| 2014/0234065 A1 * | 8/2014 | Heise | B65G 54/02 414/749.2 |
| 2014/0234949 A1 | 8/2014 | Wasson et al. | |
| 2014/0234978 A1 * | 8/2014 | Heise | B65G 54/02 436/48 |
| 2015/0014125 A1 | 1/2015 | Hecht | |
| 2015/0166265 A1 | 6/2015 | Pollack et al. | |
| 2015/0241457 A1 | 8/2015 | Miller | |
| 2015/0273468 A1 | 10/2015 | Croquette et al. | |
| 2015/0273691 A1 | 10/2015 | Pollack | |
| 2015/0276775 A1 | 10/2015 | Mellars et al. | |
| 2015/0276776 A1 | 10/2015 | Riether | |
| 2015/0276777 A1 | 10/2015 | Riether et al. | |
| 2015/0276778 A1 | 10/2015 | Riether et al. | |
| 2015/0276781 A1 | 10/2015 | Riether et al. | |
| 2015/0276782 A1 | 10/2015 | Riether | |
| 2015/0360876 A1 | 12/2015 | Sinz | |
| 2015/0360878 A1 | 12/2015 | Denninger et al. | |
| 2016/0003859 A1 | 1/2016 | Wenczel et al. | |
| 2016/0025756 A1 | 1/2016 | Pollack et al. | |
| 2016/0054341 A1 | 2/2016 | Edelmann | |
| 2016/0054344 A1 | 2/2016 | Heise et al. | |
| 2016/0069715 A1 | 3/2016 | Sinz | |
| 2016/0077120 A1 | 3/2016 | Riether | |
| 2016/0097786 A1 | 4/2016 | Malinowski et al. | |
| 2016/0229565 A1 | 8/2016 | Margner | |
| 2016/0274137 A1 | 9/2016 | Baer | |
| 2016/0282378 A1 | 9/2016 | Malinowski et al. | |
| 2016/0341750 A1 | 11/2016 | Sinz et al. | |
| 2016/0341751 A1 | 11/2016 | Huber et al. | |
| 2017/0059599 A1 | 3/2017 | Riether | |
| 2017/0096307 A1 | 4/2017 | Mahmudimanesh et al. | |
| 2017/0097372 A1 | 4/2017 | Heise et al. | |
| 2017/0108522 A1 | 4/2017 | Baer | |
| 2017/0131307 A1 | 5/2017 | Pedain | |
| 2017/0131309 A1 | 5/2017 | Pedain | |
| 2017/0131310 A1 | 5/2017 | Volz et al. | |
| 2017/0138971 A1 | 5/2017 | Heise et al. | |
| 2017/0160299 A1 | 6/2017 | Schneider et al. | |
| 2017/0168079 A1 * | 6/2017 | Sinz | G01N 35/04 |
| 2017/0174448 A1 | 6/2017 | Sinz | |
| 2017/0184622 A1 | 6/2017 | Sinz et al. | |
| 2017/0248623 A1 | 8/2017 | Kaeppeli et al. | |
| 2017/0248624 A1 | 8/2017 | Kaeppeli et al. | |
| 2017/0363608 A1 | 12/2017 | Sinz | |
| 2018/0067141 A1 | 3/2018 | Mahmudimanesh et al. | |
| 2018/0074087 A1 | 3/2018 | Heise et al. | |
| 2018/0106821 A1 | 4/2018 | Vollenweider et al. | |
| 2018/0210000 A1 | 7/2018 | van Mierlo | |
| 2018/0210001 A1 | 7/2018 | Reza | |

(56) References Cited

U.S. PATENT DOCUMENTS

| | | |
|---|---|---|
| 2018/0217174 A1 | 8/2018 | Malinowski |
| 2018/0217176 A1 | 8/2018 | Sinz et al. |
| 2018/0224476 A1 | 8/2018 | Birrer et al. |

FOREIGN PATENT DOCUMENTS

| | | |
|---|---|---|
| CN | 103608887 A | 2/2014 |
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A2 | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A2 | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

LABORATORY SAMPLE DISTRIBUTION SYSTEM AND LABORATORY AUTOMATION SYSTEM

CROSS-REFERENCE TO RELATED APPLICATIONS

This application claims priority to EP 15189525.7, filed Oct. 13, 2015, which is hereby incorporated by reference.

BACKGROUND

The present disclosure generally relates to a laboratory sample distribution system and a laboratory automation system.

Known laboratory sample distribution systems are typically used in laboratory automation systems in order to transport samples contained in sample containers between different laboratory stations.

There is a need for a laboratory sample distribution system that has optimized operating parameters.

SUMMARY

According to the present disclosure, a laboratory sample distribution system is presented. The laboratory sample distribution system can comprise a number of sample container carriers adapted to carry one or more sample containers. Each sample container carrier can comprise at least one magnetically active device. The laboratory sample distribution system can also comprise a transport plane adapted to support the sample container carriers and a number of electro-magnetic actuators stationary arranged below the transport plane. The electro-magnetic actuators can be adapted to move a sample container carrier on top of the transport plane by applying a magnetic force to the sample container carrier. Each of the electro-magnetic actuators can comprise an excitation winding and a ferromagnetic core. The excitation winding and the ferromagnetic core can be arranged such that the excitation winding surrounds the ferromagnetic core. The excitation winding vertically can exceed its assigned ferromagnetic core. The laboratory sample distribution system can also comprise a control device configured to control the movement of the sample container carriers on top of the transport plane by driving the electro-magnetic actuators such that the sample container carriers move along corresponding transport paths.

Accordingly, it is a feature of the embodiments of the present disclosure to provide for a laboratory sample distribution system that has optimized operating parameters. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
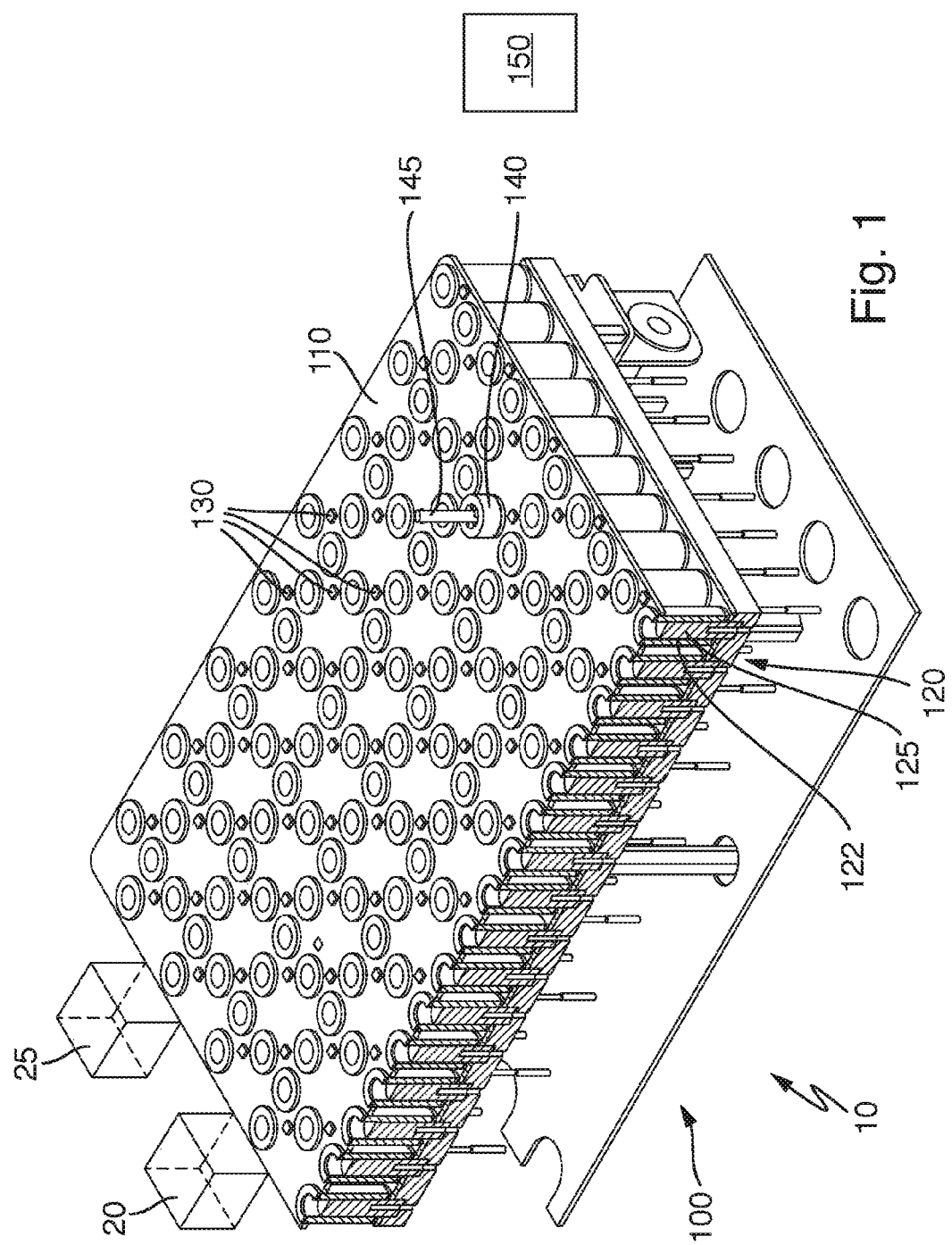
FIG. 1 illustrates a laboratory automation system comprising a laboratory sample distribution system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is presented. The laboratory sample distribution system can comprises a number (e.g. between about 2 to about 2000) of sample container carriers adapted to carry one or more sample containers. Each sample container carrier can comprise at least one magnetically active device. It can further comprise a transport plane adapted to support the sample container carriers. It can further comprise a number of electro-magnetic actuators stationary arranged below the transport plane. The electro-magnetic actuators can be adapted to move a sample container carrier on top of the transport plane by applying a magnetic drive force to the sample container carrier. Each of the electro-magnetic actuators can comprises an excitation winding and a ferromagnetic core. The excitation winding and the ferromagnetic core can be arranged such that the excitation winding can surround the ferromagnetic core. The excitation winding can exceed its assigned ferromagnetic core in a vertical direction.

According to an embodiment, the excitation winding can have a winding axis substantially perpendicular to the transport plane.

The laboratory sample distribution system can further comprise a control device configured to control the movement of the sample container carriers on top of the transport plane by driving the electro-magnetic actuators such that the sample container carriers can move along corresponding transport paths.

By use of the laboratory sample distribution system, magnetic parameters of the sample distribution system can be optimized. In particular, it has been found that magnetic fields inside an excitation winding can range higher than a respective border, or outside, of an excitation winding and that such optimized magnetic fields can be generated by reducing the length of the ferromagnetic cores with respect to the excitation windings. This can, for example, improve operation and save energy. Furthermore, a total weight can be reduced.

The sample containers can typically be designed as tubes made of glass or transparent plastic and typically can have an opening at an upper end. The sample containers can be used to contain, store and transport samples, such as blood samples or chemical samples.

The transport plane can also be denoted as transport surface. The transport plane can support the sample container carriers, which can also be denoted as carrying the sample container carriers.

The electro-magnetic actuators may be energized in order to provide for a magnetic field that can be used to move, or drive, the sample container carriers. For that purpose, the at least one magnetically active device in each sample container carrier may be a permanent magnet. Alternatively or additionally, an electromagnet can be used.

The control device can typically be a microprocessor, a microcontroller, a field-programmable gate array, a standard computer, or a similar device. In a typical embodiment, the control device can comprise a processor and storage. The program code can be stored in the storage in order to control the behavior of the processor when the storage code is executed on the processor.

The sample container carriers can typically be adapted to move in two dimensions on the transport plane. For that purpose, the electro-magnetic actuators may be arranged in two dimensions below the transport plane. The electro-magnetic actuators may be arranged in a grid, or matrix, having rows and columns along which the electro-magnetic actuators can be arranged.

According to an embodiment, respective upper ends of all excitation windings can have the same height. This can provide for a simple and scalable design.

According to an embodiment, respective upper ends of all ferromagnetic cores can have the same height. This can also provide for a simple and scalable design.

According to an embodiment, each excitation winding vertically can exceed its assigned ferromagnetic core by a distance between about 1 mm and about 3 mm. In one embodiment, each excitation winding vertically can exceed its assigned ferromagnetic core by a distance of about 2 mm.

According to an embodiment, respective upper ends of all excitation windings can be arranged between about 4.5 mm and about 6.5 mm below the transport plane. In one embodiment, respective upper ends of all excitation windings can be arranged between about about 5.5 mm below the transport plane.

According to an embodiment, each ferromagnetic core can have a vertical length between about 30 mm and about 40 mm. In one embodiment, each ferromagnetic core can have a vertical length between of about 35 mm.

According to an embodiment, each ferromagnetic core can have a substantially circular horizontal cross-section. This can allow for easy winding and handling of an electro-magnetic actuator.

According to an embodiment, each ferromagnetic core can have a diameter in its horizontal cross-section between about 7 mm and about 9 mm. In one embodiment, each ferromagnetic core can have a diameter in its horizontal cross-section of about 8 mm.

According to an embodiment, a respective air gap can be formed between each ferromagnetic core and the transport plane. Such an air gap can provide for a suitable distribution of magnetic field lines. According to an embodiment, each air gap can have a vertical extension between about 7 mm and about 8 mm, preferably about 7.5 mm. In one embodiment, each air gap can have a vertical extension of about 7.5 mm.

According to an embodiment, each excitation winding can comprise a plurality of turns. The turns can be wound directly on, or around, the assigned ferromagnetic core. This can reduce the overall dimensions of an electro-magnetic actuator.

A laboratory automation system comprising at least one laboratory station and a sample distribution system described above is presented. The laboratory station can be a pre-analytical, an analytical and/or a post-analytical station. The stations may be arranged adjacent to the laboratory sample distribution system.

Pre-analytical stations may be adapted to perform any kind of pre-processing of samples, sample containers and/or sample container carriers.

Analytical stations may be adapted to use a sample, or part of the sample, and a reagent to generate a measuring signal. The measuring signal can indicate if and in which concentration, if any, an analyte exists.

Post-analytical stations may be adapted to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

By use of the laboratory automation system, the advantages of the laboratory sample distribution system as discussed above can be made applicable for the laboratory automation system. With regard to the laboratory sample distribution system, all embodiments and variations discussed above can be applied. Advantages discussed above apply accordingly.

It can be noted that the ferromagnetic cores can be part of respective sheets, made of magnetically permeable material. The sheets can be arranged substantially in parallel such that the ferromagnetic cores are put at respective places and extend to the upper side. The sheets can be electrically isolated against each other. This can allow for an efficient production and for a suppression of eddy currents.

Referring initially to FIG. 1, FIG. 1 shows a laboratory automation system 10 comprising a first laboratory station 20, a second laboratory station 25 and a laboratory sample distribution system 100. It can be noted that the laboratory stations 20, 25 are only shown exemplarily and that typical laboratory automation systems can comprise a plurality of laboratory stations.

The laboratory sample distribution system 100 can be adapted to transport samples to and from the laboratory stations 20, 25 that can be arranged adjacent to the laboratory sample distribution system 100.

The laboratory sample distribution system 100 can comprise a transport plane 110. Below the transport plane 110, a plurality of electro-magnetic actuators 120 can be arranged. Furthermore, there can be a plurality of position sensors 130 distributed over the transport plane 110. The position sensors 130 can be embodied as Hall sensors.

The sample distribution system 100 can further comprises a plurality of sample container carriers 140. For exemplary purposes, only one sample container carrier 140 is shown in FIG. 1.

Each sample container carrier 140 can be adapted to carry a respective sample container 145. The sample container 145 can be adapted to transport a sample that is to be analyzed or otherwise handled, especially by the laboratory stations 20, 25. Each sample container carrier 140 can comprise a permanent magnet that is not visible in FIG. 1 such that the permanent magnet can interact with magnetic fields generated by the electro-magnetic actuators 120 in order to apply a magnetic driving force to the sample container carrier 140 that can move it over the transport plane 110.

The laboratory sample distribution system 100 can further comprise a control device 150, which can be connected to the electro-magnetic actuators 120 and to the position sensors 130. Thus, the control device 150 can drive the electro-magnetic actuators 120 such that magnetic fields can be generated in order to drive the sample container carriers 140 along respective transport paths simultaneously. The control device 150 can also determine the position of each sample container carrier 140 using the position sensors 130, because they can detect the magnetic field generated by the permanent magnet of the sample container carrier 140.

Each of the electro-magnetic actuators 120 can comprise an excitation winding 122 and a ferromagnetic core 125. The excitation winding 122 can surround the ferromagnetic core 125. Both the excitation winding 122 and the ferromagnetic core 125 can have a circular cross-section.

As illustrated by the electro-magnetic actuators 120 that can be arranged along a line in which the electro-magnetic actuators 120 are shown in a sectional view, each excitation winding 122 can vertically exceed its assigned ferromagnetic core 125, i.e. the ferromagnetic core 125 of the corresponding electro-magnetic actuator 120. This can allow for generation of magnetic fields having an increased magnetic field strength in the relevant regions without increasing the electric current flowing through the excitation winding 122. Thus, operating parameters and energy consumption of the laboratory sample distribution system 100 can be optimized.

The optimization can be due to the magnetic fields having an increased magnetic field strength inside the respective excitation winding 122 being free of the ferromagnetic core 125.

It can be noted that all electro-magnetic actuators 120 can be embodied the same way as those shown in sectional view, despite the fact that the relative dimensions of the other electro-magnetic actuators are not visible in FIG. 1.

Respective upper ends of all excitation windings 122 can have the same height. Accordingly, respective upper ends of all ferromagnetic cores 125 can have the same height.

Figure 2:
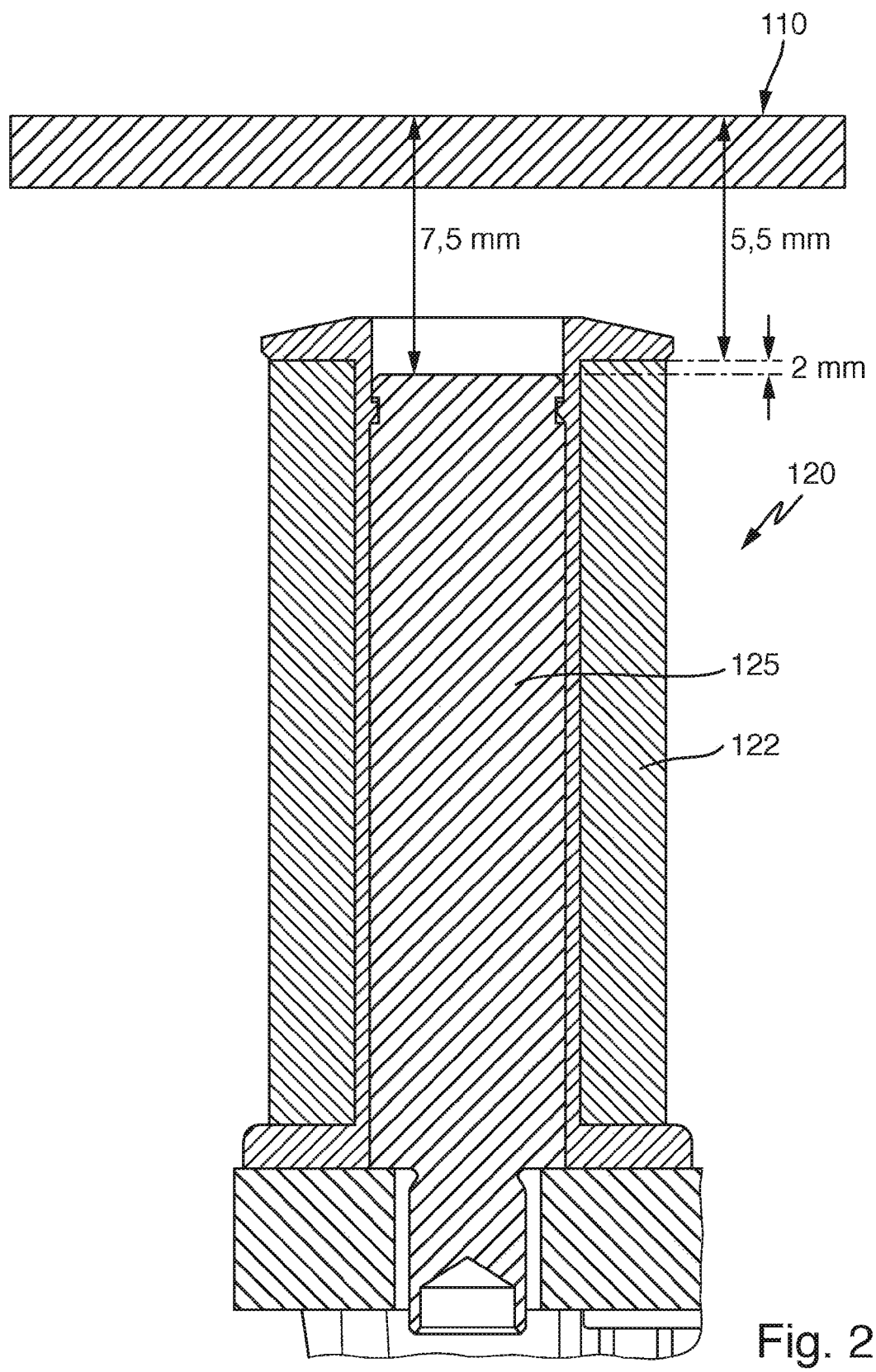
FIG. 2 illustrates a cross-sectional view of an electro-magnetic actuator comprised in the laboratory sample distribution system shown in FIG. 1 according to an embodiment of the present disclosure.

Now referring to FIG. 2, each excitation winding 122 can vertically exceed its assigned ferromagnetic core 125 by a distance of approximately 2 mm. Respective upper ends of all excitation windings 122 can be arranged approximately 5.5 mm below the transport plane 110. Each ferromagnetic core 125 can have a vertical length of approximately 35 mm. Each ferromagnetic core 125 can have a circular horizontal cross-section. Each ferromagnetic core 125 can have a diameter in its horizontal cross-section of approximately 8 mm. A respective air gap of approximately 7.5 mm can be formed between each ferromagnetic core 125 and the transport plane 110.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a plurality of sample container carriers adapted to carry one or more sample containers, wherein each sample container carrier comprises at least one magnetically active device;
   a transport plane adapted to support the sample container carriers;
   a plurality of electro-magnetic actuators stationary arranged below the transport plane, the electro-magnetic actuators adapted to move a sample container carrier on top of the transport plane by applying a magnetic force to the sample container carrier, wherein each of the electro-magnetic actuators comprises an excitation winding and a ferromagnetic core, wherein the excitation winding and the ferromagnetic core are arranged such that the excitation winding surrounds the ferromagnetic core, and wherein the excitation winding vertically exceeds its assigned ferromagnetic core; and
   a control device configured to control the movement of the sample container carriers on top of the transport plane by driving the electro-magnetic actuators such that the sample container carriers move along corresponding transport paths.

2. The laboratory sample distribution system according to claim 1, wherein respective upper ends of all excitation windings have the same height.

3. The laboratory sample distribution system according to claim 1, wherein respective upper ends of all ferromagnetic cores have the same height.

4. The laboratory sample distribution system according to claim 1, wherein each excitation winding vertically exceeds its assigned ferromagnetic core by a distance (D1).

5. The laboratory sample distribution system according to claim 4, wherein the distance (D1) is between 1 mm and 3 mm.

6. The laboratory sample distribution system according to claim 4, wherein the distance (D1) is 2 mm.

7. The laboratory sample distribution system according to claim 1, wherein respective upper ends of all excitation windings are arranged between 4.5 mm and 6 mm below the transport plane.

8. The laboratory sample distribution system according to claim 1, wherein respective upper ends of all excitation windings are arranged 5.5 mm below the transport plane.

9. The laboratory sample distribution system according to claim 1, wherein each ferromagnetic core has a vertical length between 30 mm and 40 mm.

10. The laboratory sample distribution system according to claim 1, wherein each ferromagnetic core has a vertical length of 35 mm.

11. The laboratory sample distribution system according to claim 1, wherein each ferromagnetic core has a circular horizontal cross-section.

12. The laboratory sample distribution system according to claim 1, wherein each ferromagnetic core has a diameter in its horizontal cross-section between 7 mm and 9 mm.

13. The laboratory sample distribution system according to claim 1, wherein each ferromagnetic core has a diameter in its horizontal cross-section of 8 mm.

14. The laboratory sample distribution system according to claim 1, further comprises, a respective air gap is formed between each ferromagnetic core and the transport plane.

15. The laboratory sample distribution system according to claim 14, wherein each air gap has a vertical extension between 7 mm and 8 mm.

16. The laboratory sample distribution system according to claim 14, wherein each air gap has a vertical extension of 7.5 mm.

17. The laboratory sample distribution system according to claim 1, wherein each excitation winding comprises a plurality of turns.

18. The laboratory sample distribution system according to claim 17, wherein the turns are wound directly on the assigned ferromagnetic core.

19. A laboratory automation system, the laboratory automation system comprising:
    at least one laboratory station; and
    a sample distribution system according to claim 1.

20. The laboratory automation system according to claim 19, wherein the at least one laboratory station is a pre-analytical, an analytical and/or a post-analytical station.

\* \* \* \* \*